US00PP27426P2

(12) United States Plant Patent
Danziger

(10) Patent No.: US PP27,426 P2
(45) Date of Patent: Nov. 29, 2016

(54) ***CARYOPTERIS* 'CT-9-12'**

(50) Latin Name: *Caryopteris clandonensis*
Varietal Denomination: CT-9-12

(71) Applicant: Gavriel Danziger, Mishmar Hashiva (IL)

(72) Inventor: Gavriel Danziger, Mishmar Hashiva (IL)

( * ) Notice: Subject to any disclaimer, the term of this patent is extended or adjusted under 35 U.S.C. 154(b) by 0 days.

(21) Appl. No.: 14/545,937

(22) Filed: Jul. 8, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Jul. 23, 2016.*

* cited by examiner

*Primary Examiner* — Annette Para
(74) *Attorney, Agent, or Firm* — Cassandra Bright

(57) ABSTRACT

A new and distinct *Caryopteris* cultivar named 'CT-9-12' is disclosed, characterized by uniquely upright stems, shiny leaves and compact growth habit. The new variety is a *Caryopteris*, normally produced as an outdoor garden or container plant.

3 Drawing Sheets

Latin name of the genus and species: *Caryopteris clandonensis*.

Variety denomination: 'CT-9-12'.

BACKGROUND OF THE INVENTION

The new *Caryopteris* cultivar is a product of a planned breeding program conducted by the inventor, Gavriel Danziger, in Moshav Mishmar Hashiva, Israel. The objective of the breeding program was to produce new *Caryopteris* varieties for ornamental commercial applications. The cross resulting in this new variety was made during 2008.

The seed parent is the unpatented, proprietary variety referred to as *Caryopteris* 'CT-Z-4'. The pollen parent is unknown as it was an open pollination breeding program. The new variety was discovered in 2009 by the inventor in a group of seedlings resulting from the 2008 crossing in a research greenhouse in Moshav Mishmar Hashiva, Israel.

Asexual reproduction of the new cultivar was performed by vegetative terminal cuttings. This was first performed at a research greenhouse in Moshav Mishmar Hashiva, Israel in 2009 and has shown that the unique features of this cultivar are stable and reproduced true to type in more than 17 to 20 successive generations.

SUMMARY OF THE INVENTION

The cultivar 'CT-9-12' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CT-9-12' These characteristics in combination distinguish 'CT-9-12' as a new and distinct *Caryopteris* cultivar:

1. Uniquely compact plant form.
2. Upright stem growth.
3. Shiny leaves.

Plants of the new cultivar 'CT-9-12' are similar to plants of the seed parent, *Caryopteris* 'CT-Z-4' in most horticultural characteristics, however, plants of the new cultivar 'CT-9-12' differ in the following;

1. More compact in form.
2. Upright stem growth, seed parent has stems bending downward, and in various irregular positions.

COMMERCIAL COMPARISON

Plants of the new cultivar 'CT-9-12' are comparable to the unpatented commercial variety *Caryopteris* 'Kew Blue' The two *Caryopteris* varieties are similar in most horticultural characteristics; however, the new variety 'CT-9-12' differs in the following:

1. More compact in plant form.
2. Upright stems, the comparator has stems bending downward, and in various irregular positions.

Plants of the new cultivar 'CT-9-12' can also be compared to the unpatented commercial variety *Caryopteris* 'Dark Knight'. The two *Caryopteris* varieties are similar in most horticultural characteristics; however the new variety 'CT-9-12' differs in the following:

1. Leaves are darker green in color.
2. Fuller compact plant habit, the comparator is less compact and more loose and open in habit.

BRIEF DESCRIPTION OF THE PHOTOGRAPHS

The accompanying photograph in FIG. 1 illustrates in full color a typical plant of 'CT-9-12' grown outdoors in the ground. Age of the plant photographed is approximately 2-3 years old from a rooted cutting.

Figure 1:
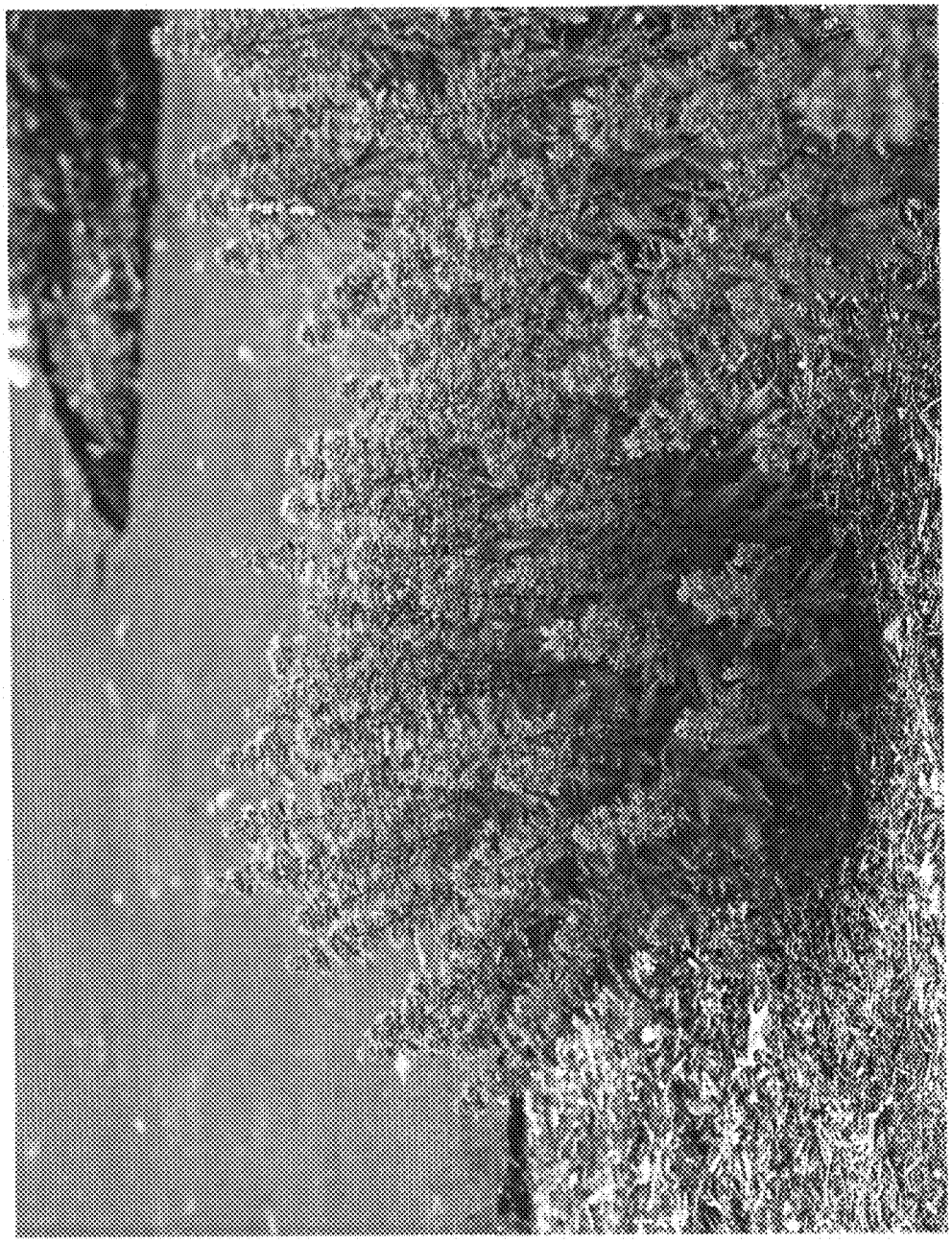
Figure 2:
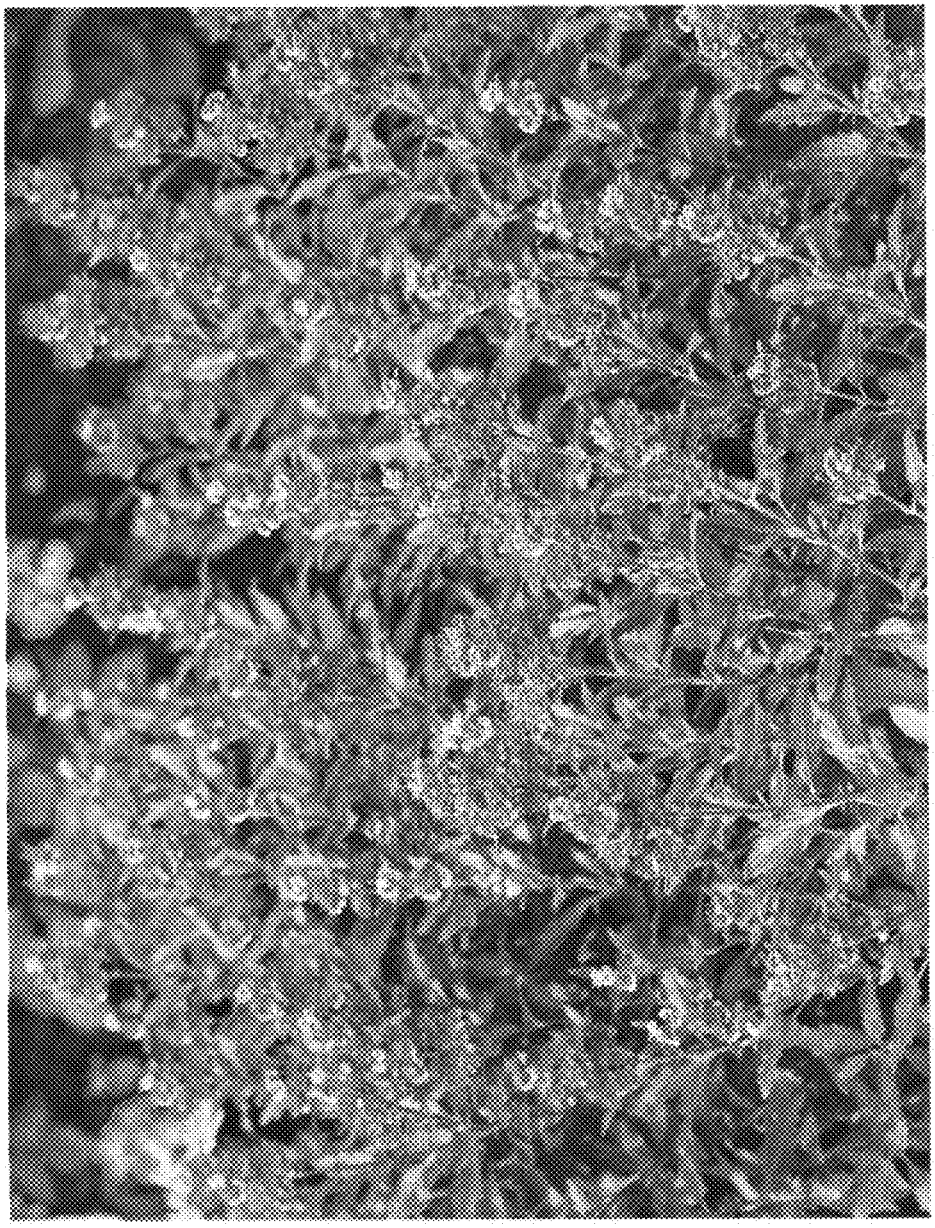
FIG. 2 illustrates a close up of the inflorescence.
Figure 3:
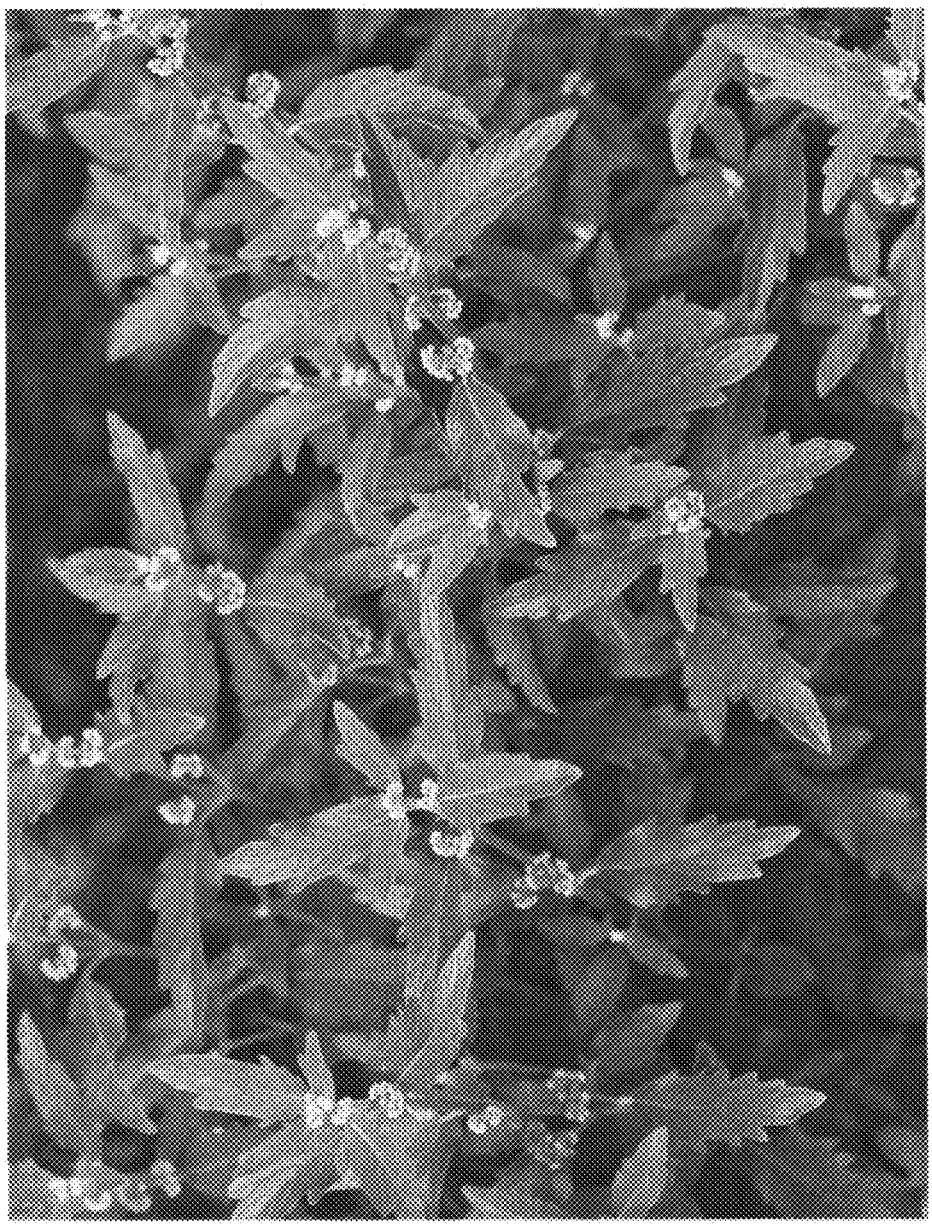
FIG. 3 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'CT-9-12' plants grown in June in moderate climate in a greenhouse, in Grand haven, Mich. USA. The growing temperature ranged from 29° C. to 31° C. during the day and from 18° C. to 21° C. during the night. The variety was maintained in greenhouse in pots under UV transparent nets. General light conditions are normal sunlight and numerical values represent averages of typical plant types. First pinch date between 4-6 weeks, secondary pinching between 8-10 weeks.

Botanical classification: *Caryopteris clandonensis* 'CT-9-12'.

PROPAGATION

Type of propagation typically used: Cutting.

Time to initiate roots: 7-14 days in Summer at 25-30° C. 14-21 days in Winter at 18-23°.

Time to produce a rooted cutting or liner: 17-24 days in Summer at 25-30° C. 22-27 days in Winter at 18-23°.

Root description: Fine, fibrous roots, not dense very spacious light brown-white in color.

PLANT

Age of plant described: Approximately 2-3 years from rooted cutting.

Plant type: Perennial shrub.

Container size of the plant described: #3.

Appropriate containers: 1, 2, 3, 5 gallon commercial containers.

Growth habit: Upright/Mounded.

Height: Approximately 64 cm.

Plant spread: Approximately 92 cm.

Growth rate: Moderate.

Plant vigor: Moderate.

Characteristics of primary lateral branches:

- *Quantity.*—85.
- *Branching habit.*—Upright/semi-compact, basal branching pinching required, round branches.
- *Length.*—50-64 cm.
- *Diameter.*—5-8 cm.
- *Color.*—New growth/tips: RHS Greyed-orange 177A turning to Yellow-green 144B and Yellow-green 152B. Mature growth: Near RHS Grey-brown 199D.
- *Pubescence.*—Very little pubescence on new growth.
- *Stem aspect/angle.*—35-45°.
- *Strength.*—Strong/moderate.

Internode length: About 2-3 cm.

FOLIAGE

Leaf:

- *Arrangement.*—Opposite, single.
- *Quantity.*—Approximately 60 per branch.
- *Average length.*—4.5 cm.
- *Average width.*—1.5 cm.
- *Shape.*—Oblanceolate.
- *Apex.*—Obtuse.
- *Base.*—Cuneate.
- *Margin.*—Lobed.
- *Texture of top surface.*—Smooth, silky.
- *Texture of bottom surface.*—Smooth, velvety.
- *Pubescence.*—None.
- *Color.*—Young foliage upper side: RHS Green 139A. Young foliage under side: RHS Yellow-green 148B. Mature foliage upper side: RHS Green 139A. Mature foliage under side: RHS Yellow-green 148B.
- *Venation.*—Type: Pinnate. Venation color upper side: Near RHS Yellow-green 148B. Venation color under side: Near RHS Yellow-green 148B.
- *Petiole.*—Length: 1 cm. Diameter: 0.1 cm. Color: Upper side: RHS Yellow-green 147B. Lower side: RHS Yellow-green 144B.
- *Texture.*—Upper side: Smooth, Slightly pubescent. Lower side: Smooth, Slightly pubescent.

FLOWER

Flower arrangement: Small single flowers arranged on axillary cymes.

Flower shape: Zygomorphic.

Natural flowering season: Spring-early Summer.

Number of days to flowering (response time): 2-3 weeks.

Inflorescence and flower type and habit: Cyme, rotate.

Rate of flower opening: Moderate.

Flower longevity on plant: 3-4 weeks.

Persistent or self-cleaning: Self-cleaning.

Quantity of flowers per lateral stem: ~250.

Quantity of flowers per inflorescence: ~40.

Quantity of flowers per plant: ~21,000.

Bud:

- *Shape.*—Round.
- *Length.*—2 mm.
- *Diameter.*—2 mm.
- *Color.*—RHS Yellow-green 148B.

Flower size:

- *Diameter.*—7 mm.
- *Length.*—8 mm.

Petals:

- *Appearance.*—Small; 1-2 petals contain 8+ spurs towards tip of the petal.
- *Arrangement.*—Whorled, fused.
- *Petal length.*—7 mm.
- *Petal width.*—5-7 mm.
- *Quantity.*—5-6.
- *Texture.*—Smooth.
- *Apex.*—Emerginate and spurred.
- *Shape.*—Obovate and spurred.
- *Base.*—Subulate.
- *Margin.*—Entire.
- *Aspect.*—Upright/outward.

Petal color:
*When opening*.—Upper surface: RHS Violet-blue 89D. Lower surface: RHS Violet-blue 89D.
*Fully opened*.—Upper surface: RHS Violet-blue 89D. Lower surface: RHS Violet-blue 89D.
*Fading to color*.—Upper and lower: RHS Violet-blue 95C.
Sepals:
*Quantity per flower*.—6.
*Shape*.—Small, linear.
*Length*.—4 mm.
*Width*.—3 mm.
*Apex*.—Acute.
*Base*.—Fused.
*Margin*.—Entire.
*Texture*.—Upper: Smooth. Lower: Smooth, slightly pubescent.
*Color*.—Upper Surface: RHS Green 137C. Lower Surface: RHS Yellow-green 147B.
Calyx:
*Shape*.—Radial/linear.
*Length*.—3 mm.
*Diameter*.—2 mm.
Peduncle:
*Length*.—2.5 cm.
*Diameter*.—1.5 mm.
*Angle*.—~35°.
*Strength*.—Moderate/weak.
*Texture*.—Smooth, slightly pubescent.
*Color*.—RHS Yellow-green 144A.
Pedicel:
*Length*.—1.5 cm.
*Diameter*.—0.1 cm.
*Color*.—RHS Yellow-green 144A.
*Angle*.—~35°.
*Texture*.—Smooth, slightly pubescent.

REPRODUCTIVE ORGANS

Stamens:
*Number*.—5.
*Filament length*.—1 cm.
*Filament color*.—RHS Yellow-green 144A.
Anthers:
*Shape*.—Round.
*Length*.—1 mm.
*Color*.—RHS Violet-blue 95B.
*Pollen*.—Color: RHS Violet-blue 95A. Quantity: Little.
Pistil:
*Number*.—1.
*Length*.—1 cm.
*Style*.—Length: 1 cm. Color: RHS Violet 87C.
*Stigma*.—Shape: Acute. Color: RHS Violet 87C. Ovary Color: RHS Yellow-green 145A.

OTHER CHARACTERISTICS

Disease/pest resistance: Tolerance for *Prodenia* and *Botrytis*. Resistance to other typical pests and pathogens of *Caryopteris*.
Temperature tolerance: −26° C. lowest temperature tolerant, likely to tolerate colder. Highest temperature tolerant to 35° to 40° C.
Garden performance: Needs well drained soil.
What is claimed is:
1. A new and distinct cultivar of *Caryopteris* plant named 'CT-9-12' as herein illustrated and described.

* * * * *